United States Patent [19]

Kimura et al.

[11] Patent Number: 4,902,649
[45] Date of Patent: Feb. 20, 1990

[54] HARD TISSUE SUBSTITUTE COMPOSITION

[75] Inventors: Yoshitaka Kimura, Tokyo; Yuji Furuta, Shiojiri; Kunihiro Miyazaki, Shiojiri; Tadashi Hiraiwa, Shiojiri, all of Japan

[73] Assignee: Showa Denko Kabushiki Kaisha, Tokyo, Japan

[21] Appl. No.: 94,781

[22] Filed: Sep. 10, 1987

[30] Foreign Application Priority Data

Sep. 10, 1986 [JP] Japan .................................. 61-211733
Nov. 1, 1986 [JP] Japan .................................. 61-259617

[51] Int. Cl.$^4$ .............................................. C04B 35/00
[52] U.S. Cl. .......................................... 501/1; 106/35; 606/99
[58] Field of Search ............................. 501/1; 623/16; 128/92 VP, 92 W; 106/35

[56] References Cited

U.S. PATENT DOCUMENTS

| 3,982,543 | 9/1976 | Schmitt et al. | 128/335.5 |
| 4,113,500 | 9/1978 | Ebihara et al. | 106/39.5 |
| 4,141,864 | 2/1979 | Rijke et al. | 260/17.4 |
| 4,192,021 | 3/1980 | Deibig et al. | 623/16 X |
| 4,207,306 | 6/1980 | Jarcho | 423/633 |
| 4,268,639 | 5/1981 | Seidel et al. | 525/303 |
| 4,376,168 | 3/1983 | Takami et al. | 501/1 |
| 4,457,028 | 7/1984 | Draenert | 128/92 VP X |
| 4,518,430 | 5/1985 | Brown et al. | 106/35 |
| 4,550,449 | 11/1985 | Tunc | 623/16 |
| 4,554,686 | 11/1985 | Baker et al. | 623/16 |
| 4,610,692 | 9/1986 | Eitenmuller et al. | 623/16 |
| 4,629,464 | 12/1986 | Takata et al. | 623/16 |
| 4,645,503 | 2/1987 | Lin et al. | 623/16 |
| 4,661,530 | 5/1987 | Gogolewski et al. | 521/137 |
| 4,661,536 | 4/1987 | Dorman et al. | 523/113 |
| 4,693,986 | 9/1987 | Vit et al. | 501/1 |
| 4,719,149 | 1/1988 | Aasen et al. | 106/35 |

FOREIGN PATENT DOCUMENTS 59-182263 of 1984 Japan.
60-253454 of 1985 Japan.
61-71060 of 1986 Japan.
61-68054 4/1986 Japan.

Primary Examiner—Brian E. Hearn
Assistant Examiner—Andrew Griffis
Attorney, Agent, or Firm—Sughrue, Mion, Zinn, Macpeak & Seas

[57] ABSTRACT

A composition for use in forming a hard tissue substitute comprising (A) a powder ingredient mainly comprised of $Ca_{n+2}(PO_4)_2O_{n-1}$, where n is from 1.9 to 4.9 and (B) an aqueous solution of an organic acid, preferably of the TCA cycle, or a polymer of an organic acid. This composition has a good affinity with living organisms, a high compressive strength, and a low disintegration rate.

16 Claims, No Drawings

HARD TISSUE SUBSTITUTE COMPOSITION

BACKGROUND OF THE INVENTION

1. Field of the Invention

The present invention relates to a composition which is used as a substitute for hard tissue of a human body (Hereinafter called hard tissue substitute composition.).

2. Description of the Related Art

Compositions comprising a powder ingredient and a liquid ingredient are widely used as a substitute for hard tissue of a human body, and include bone cements, such as a methyl methacrylic-based bone cement, in the medical field, and a root canal filling material or various dental cements, such as cements for bonding, filling, back lining or sealing, in the dental field. These compositions or materials are mainly comprised of a natural or synthetic resin and an inorganic material, and have the drawback of causing adverse effects on living organisms. That is, conventional hard tissue substitute compositions often stimulate organisms and have a poor affinity with an organism due to the heterogeniety of the composition obtained from the material of an organism. Thus, a hard tissue substitute composition without stimulus and pyrexia and having an excellent workability has been sought.

As a material having compatibility with an organism, hydroxy apatite (HAP) and α-tricalcium phosphate (α-TCP) are known (Japanese Unexamined Patent Publication (Kokai) Nos. 59-182263, 60-253454 and 61-71060). However, hydroxy apatite can not be hardened even if mixed with an organic acid solution or an aqueous physiological sodium chloride solution, although α-TCP can be hardened when mixed with an organic acid or with water. However, although a hardened α-TCP has a sufficient compressive strength, the disintegration rate of the hardened α-TCP is high, more than 2%, and this is a drawback. The term "disintegration rate" means the rate of the weight reduction of a mass immersed in water at 37° C. for 24 hours (Japanese Industrial Standard (JIS)-T6602).

As a filling agent for filling cavities resulting from periodontitis, a granule of β-TCP and a hardning mixture of α-TCP and a polyacrylic acid are known. However, the former has poor filling and workability and the latter has a high rate of disintegration.

SUMMARY OF THE INVENTION

The main object of the present invention is to provide a hard tissue substitute composition having an affinity with an organism without stimulation and able to be hardened to a hard mass with an appropriate handling or setting time period for various usages.

The above object is attained by a hard tissue substitute composition comprising a powder ingredient mainly composed of $Ca_{n+2}(PO_4)_2O_{n-1}$ where n is from 1.9 to 4.8 and a liquid ingredient based on an organic acid or a polymer of an organic acid.

DESCRIPTION OF THE PREFERRED EMBODIMENTS

The characteristic features of the present invention are the use of a particular calcium phosphate as a powder ingredient and the use of an organic acid preferably of the tricarboxylic acid cycle (TCA cycle, also referred by as "citric acid cycle") or a polymer thereof as a main component of a liquid ingredient.

As is well known, inorganic components of biological hard tissue such as bones and teeth comprise calcium phosphates such as hydroxy apatite and brushite. Recently, inorganic materials which are similar to the above biomaterials have attracted attention because of the safety factor thereof toward a living organism. Such inorganic biomaterials are classified into bioactive and bioinert materials depending on the activity at the interface with living organisms The calcium phosphate used in the present invention is an inorganic material having an affinity with an organism, which affinity is comparable to that of hydroxy apatite. This calcium phosphate is characterized by a bone substituting property due to disintegration in a living organism. It is known that this calcium phosphate is bioactive and is converted to hydroxy apatite under certain conditions.

To enable the use of a material such as cement as a substitute for hard tissue, in practice, a mixture of a calcium phosphate and a liquid ingredient must be hardened to a hard mass, and the hardened mass should be neutral or nearly neutral and should not be disintegrated. A serious investigation into these factors has not been made, but it has been found that, although α-TCP can be hardened with an organic acid, the disintegration rate thereof is high and due to a high acidity it may cause inflammation in a living organism.

The hard tissue substitute composition of the present invention is hardenable to a hard mass, has a low distingration rate, and has a neutral or nearly neutral pH.

The calcium phosphate used in the present invention has a chemical formula: $Ca_{n+2}(PO_4)_2O_{n-1}$ where n is from 1.9 to 4.8. When n is from 1.9 to 2.1, the calcium phosphate is tetracalcium phosphate. If n is less than 1.9, the acidity of the composition is too high, and n is larger than 4.8, the basicity of the composition is too high. Neither case is suitable as a biomaterial. The above calcium phosphate used in the present invention may contain other calcium phosphates or the like such as tricalcium phosphate, hydroxy apatite, and calcium oxide in an small amount, but should preferably comprise 80% by weight or more of the calcium phosphate having the formula of $Ca_{n+2}(PO_4)_2O_{n-1}$.

The calcium phosphate having the above formula can be produced, for example, by the following chemical reaction:

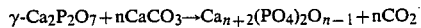

$$\gamma\text{-}Ca_2P_2O_7 + nCaCO_3 \rightarrow Ca_{n+2}(PO_4)_2O_{n-1} + nCO_2$$

where $\gamma\text{-}Ca_2P_2O_7$ and $CaCO_3$ are mixed in a ratio wherein n is from 1.9 to 4.8. $CaCO_3$ may be replaced by CaO, etc. The reaction temperature is suitably in a range of 1200° to 1700° C. The resultant calcium phosphate can be expressed by the formula $Ca_{n+2}(PO_4)_2O_{n-1}$, but may contain tricalcium phosphate, hydroxy apatite, calcium oxide, etc., in a small amount, depending on various conditions of the reaction such as heating temperature, temperature elevation rate, humidity content in a cooling air introduced after heating, etc. A mixture of the starting materials may be shaped under a pressure of, e.g., more than 0.1 ton/cm², by a rubber or mold press method before heating at 1200° C. or more. The thus-obtained compression molded calcium phosphate has a higher bulk density and a higher compressive strength.

The powder ingredient of the present invention should preferably have a particle size of about 44 μm or less.

The powder ingredient may contain additives such as X-ray image media, if necessary.

The liquid ingredient used in the present invention is based on an organic acid which is preferably an organic acid other than those of the TCA cycle, such as, malonic acid, tartaric acid, lactic acid, pyruvic acid, oxalic acid, acrylic acid, maleic acid and itaconic acid. acid, maleic acid, fumaric acid, oxalic acid and itaconic acid. The liquid ingredient may be a polymer of an organic acid or of an unsaturated monomer having a carboxilic group. The polymer may be a homopolymer or a copolymer. The organic acid is preferably contained in an amount of 25 to 60% by weight of the liquid ingredient. Less than 25% by weight of an organic acid may not be sufficient for completion of the chemical reaction, resulting in an incomplete setting of the composition, and more than 60% by weight of an organic acid sacrifices the workability (setting time), which is extremely important for a hard tissue substitute composition, and further, results in a too hard mixture of the powder and liquid ingredients, making handling thereof difficult.

The liquid ingredient may contain an inorganic acid such as phosphoric acid or chloric acid in a small amount, for example, 0.5 to 5% by weight of the liquid ingredient, in order to improve the properties, particularly, compressive strength of a hardened composition.

The liquid ingredient is preferably an aqueous solution.

The liquid ingredient may contain additives such as a water-soluble calcium salt, and a pH adjuster, if necessary.

The mixing ratio of the powder and liquid ingredients is 1.0 to 2.2 parts by weight of the powder ingredient per part by weight of the liquid ingredient, if the liquid ingredient contains 25 to 60% by weight of an organic acid or a polymer thereof, as mentioned before. A lesser amount of the powder ingredient results in a too long hardening time and a greater amount of the powder ingredient makes mixing of the composition difficult.

The following shows a typical recipe (by weight) of the powder and liquid ingredients of a hard tissue substitute composition of the present invention.

TABLE I

| Powder ingredient: | |
|---|---|
| $Ca_{n+2}(PO_4)_2O_{n-1}$ : n = 2.0 − 4.8 | 70–100% |
| X-ray image media | less than |
| ($BaSO_4$, $CHI_3$, $Na_2FPO_3$, $CaF_2$) | 30% |
| Liquid ingredient: | |
| TCA-cycle organic acid | 25 to 60% |
| (citric, succinic malic acids etc.) | |
| Purified water | 35 to 70% |
| Additives | 0 to 5% |

The hard tissue substitute composition of the present invention can be used as described below, since it can have an appropriate operation margin or hardening time for various usages and be hardened promptly in a living organism to a hard mass.

In the medical field, it can be used as bone cements for bonding or filling between an autogeneous bone and an artificial bone or joint. It can be also used as a substitute bone when filled in a deficient portion of a bone in the form of a fluid mud comprising the powder and liquid ingredients.

In the dental field, it can be used mainly for bonding or filling, but may be used for back lining or sealing due to its excellent affinity with an organism.

In this embodiment, a composition comprising a powder ingredient mainly comprised of a tetracalcium phosphate and a liquid ingredient based on an organic compound having a carboxylic group or a polymer thereof may be preferably used as a filling composition for bone or teeth. This composition has a relatively high compressive strength (higher than 700 kg/cm$^2$), a low disintegration rate (less than 1 wt%), a good affinity with a living organism, and a good workability.

The present invention is now described with reference to the following examples.

EXAMPLES 1 TO 7

Powdered calcium carbonate ($CaCO_3$) and powdered $\gamma$-calcium pyrophosphate ($\gamma$-$Ca_2P_2O_7$) were mixed in a mole ratio shown in Table II. The mixture was heated in air at a temperature elevation rate of 20° C./min to a temperature shown in Table II, kept at that temperature for 2 hours, and then cooled at a temperature reduction rate of 40° C./min. The resultant $Ca_{n+2}(PO_4)_2O_{n-1}$ mass was crushed and milled in a ball mill, and then screened with a 44 $\mu$m sieve to obtain a powder having an average particle size shown in Table II.

TABLE II

| Example No. | Mole Ratio of $CaCO_3$/$\gamma$-$Ca_2P_2O_7$ | Heating Temp. (°C.) | Average Particle Size ($\mu$m) |
|---|---|---|---|
| 1 | 2.0 | 1250° C. | 6.8 $\mu$m |
| 2 | 2.0 | 1350° C. | 7.2 $\mu$m |
| 3 | 2.5 | 1450° C. | 6.6 $\mu$m |
| 4 | 3.0 | 1500° C. | 7.5 $\mu$m |
| 5 | 3.5 | 1550° C. | 7.2 $\mu$m |
| 6 | 4.5 | 1600° C. | 6.2 $\mu$m |
| 7 | 4.8 | 1650° C. | 5.8 $\mu$m |

The resultant calcium phosphate, which can be expressed as a formula $Ca_{n+2}(PO_4)_2O_{n-1}$, was mixed with an aqueous solution of 40% citric acid and 10% tartaric acid (water content: 50%) in a weight ratio of powder/liquid of 1.5 and hardened at an ambient temperature. The times needed for hardening are shown in Table III.

The thus-obtained hardened bodies were subject to measurements of the compressive strength under JIS-T6602, the disintegration rate under JIS-T6602, and the pH. The results are shown in Table III.

TABLE III

| Example No. | Powder Ingredient No. | Setting Time (min) | Compressive Strength (kg/cm$^2$) | pH of Solution (%) |
|---|---|---|---|---|
| 1 | 1 | 6.5 | 1420 | 6.98 |
| 2 | 2 | 5.0 | 1340 | 6.92 |
| 3 | 3 | 5.5 | 1180 | 7.03 |
| 4 | 4 | 7.0 | 1260 | 7.04 |
| 5 | 5 | 6.5 | 1110 | 7.10 |
| 6 | 6 | 6.0 | 1060 | 6.96 |
| 7 | 7 | 5.5 | 1140 | 6.92 |

EXAMPLE 8

Powdered calcium carbonate and powdered $\gamma$-calcium pyrophosphate were mixed in a mole ratio of 2 to 1, which was heated at 1250° C. for 3 hours. After cooling, the resultant tetracalcium phosphate was milled and sieved with a 44 $\mu$m screen. The resultant undersieve powder was mixed with an aqueous solution of a copolymer (mean molecular weight of 30,000) of 85 wt% acrylic acid and 15 wt% itaconic acid (water content: 50 wt%) in a powder/liquid weight ratio of 1.5, and hardened at an ambient temperature.

The hardened body had a compressive strength of 750 kg/cm² under JIS-T6602 and a disintegration rate of 0.5 wt%.

The above hardening mixture was implanted in a marrow of a femur of a rate and a pathological observation thereof was carried out. As a result, substantially no inflamed cells were observed, foreign body rejection was slight, and the formation of bone began in 3 to 4 days. These results are comparative with those of α-TCP which has a good organism affinity.

EXAMPLE 9 (Comparative)

Powdered calcium carbonate and powdered γ-calcium pyrophosphate were mixed in a mole ratio of 1 to 1, heated at 1250° C. for 3 hours to form α-TCP, which was milled and seived with a 44 μm screen. From the resultant undersieve powder, a hardened body was obtained by the same procedure as used in Example 8.

The hardened body had a compressive strength of 950 kg/cm² and a disintegration rate of 2.1 wt%.

We claim:

1. A composition which is hardenable by a chelate reaction for use in forming a hard tissue substitute in situ comprising:
   (A) a powder ingredient mainly comprised of $Ca_{n+2}(PO_4)_2O_{n-1}$ where n is from 1.9 to 4.8, and
   (B) an aqueous solution of an organic acid or a polymer thereof,
wherein said aqueous solution (B) comprises from 25 to 60% by weight of said organic acid or polymer thereof, and wherein the composition is mixed in a ratio of 1.0 to 2.2 parts by weight of said powder ingredient (A) per 1.0 part by weight of said aqueous solution (B).

2. A composition according to claim 1, wherein said powder ingredient additionally comprises tricalcium phosphate, hydroxy apatite and calcium oxide.

3. A composition according to claim 2, wherein said powder ingredient comprises more than 80% by weight of $Ca_{n+2}(PO_4)_2O_{n-1}$.

4. A composition according to claim 1, wherein said powder ingredient has a diameter of less than about 44 μm.

5. A composition according to claim 1, wherein said powder ingredient further comprises an X-ray contrast media.

6. A composition according to claim 1, wherein said aqueous solution comprises an organic acid of the tricarboxylic acid cycle of a human body.

7. A composition according to claim 6, wherein said organic acid of the tricarboxylic acid cycle of the human body is selected from the group consisting of citric acid, malic acid, and aspartic acid.

8. A composition according to claim 1, wherein said aqueous solution comprises an organic acid other than those of the tricarboxylic acid cycle.

9. A composition according to claim 1, wherein said aqueous solution comprises a polymer of an unsaturated monomer having a carboxylic group.

10. A composition according to claim 1, wherein said aqueous solution includes an inorganic acid selected from the group consisting of phosphoric acid and a chloric acid.

11. A composition according to claim 10, wherein said aqueous solution includes 0.5 to 5% by weight of said inorganic acid.

12. A composition according to claim 1, wherein said tetracalcium phosphate has a chemical formula of $Ca_{n+2}(PO_4)_2O_{n-1}$ where n is from 1.9 to 2.2.

13. A composition according to claim 8, wherein said organic acid other than those of the tricarboxylic acid cycle of the human body is selected from the group consisting of malonic acid, tartaric acid, lactic acid, pyruvic acid, oxalic acid, acrylic acid, maleic acid and itaconic acid.

14. A composition according to claim 1, wherein said composition is hardened at ambient temperature.

15. A composition which is hardenable by a chelate reaction for use in forming a hard tissue substitute in situ comprising:
   (A) a powder ingredient mainly comprised of tetracalcium phosphate, and
   (B) an aqueous solution of an organic acid or a polymer thereof,
wherein said aqueous solution (B) comprises from 25 to 60% by weight of said organic acid or polymer thereof, and wherein the composition is mixed in a ratio of 1.0 to 2.2 parts by weight of said powder ingredient (A) per 1.0 part by weight of said aqueous solution (B).

16. A composition according to claim 15, wherein said composition is hardened at ambient temperature.

* * * * *